US012576264B2

(12) United States Patent
Rhaburn

(10) Patent No.: US 12,576,264 B2
(45) Date of Patent: Mar. 17, 2026

(54) NEUROPROSTHESIS APPARATUS FOR STIMULATING LEG MOVEMENT

(71) Applicant: Jamantha Rhaburn, Las Vegas, NV (US)

(72) Inventor: Jamantha Rhaburn, Las Vegas, NV (US)

( * ) Notice: Subject to any disclaimer, the term of this patent is extended or adjusted under 35 U.S.C. 154(b) by 343 days.

(21) Appl. No.: 18/201,164

(22) Filed: May 23, 2023

(65) Prior Publication Data

US 2024/0390666 A1     Nov. 28, 2024

(51) Int. Cl.
A61N 1/04          (2006.01)
A61N 1/36          (2006.01)

(52) U.S. Cl.
CPC ......... A61N 1/0456 (2013.01); A61N 1/0484 (2013.01); A61N 1/36034 (2017.08)

(58) Field of Classification Search
None
See application file for complete search history.

(56) References Cited

U.S. PATENT DOCUMENTS 4,697,808 A * 10/1987 Larson ................. A61H 1/0237
                                                                    482/901
5,020,790 A     6/1991 Beard 5,961,541 A     10/1999 Ferrati
7,963,932 B2     6/2011 Ashihara
10,814,131 B2 * 10/2020 Goldwasser ......... A61N 1/0492
11,123,556 B2 *  9/2021 Coleman ............ A61N 1/36014
11,324,655 B2 *  5/2022 De Rossi ............ A61H 1/0266
2006/0260620 A1 11/2006 Kazerooni
2012/0330375 A1 * 12/2012 Nathan ................ A61N 1/0452
                                                                    607/48

FOREIGN PATENT DOCUMENTS

WO     WO2009082249     7/2009

* cited by examiner

*Primary Examiner* — Carl H Layno
*Assistant Examiner* — Bryan Mcallister Lee

(57)                    ABSTRACT

A neuroprosthesis apparatus for stimulating leg movement in a user via functional electrical stimulation includes a waistband and a pair of leg attachment members. Each leg attachment member is coupled to and extends downwardly from the waistband. A user wears the apparatus with the waistband extending around the user's body and each leg attachment member attaching to one of the legs of the user. An electrical stimulator comprises a plurality of electrodes that is dispersed along each leg attachment member. The electrodes selectively transmit electrical current through a skin of the user to efferent nerves to induce muscle contractions and enable movement of the legs and feet of a user experiencing paralysis.

20 Claims, 5 Drawing Sheets

NEUROPROSTHESIS APPARATUS FOR STIMULATING LEG MOVEMENT

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to prostheses and more particularly pertains to a new prosthesis for stimulating leg movement in a user via functional electrical stimulation.

(2) Description of Related Art Including Information Disclosed Under 37 CFR 1.97 and 1.98

The prior art relates to prostheses including devices which brace the legs of a user and devices which attach to the legs of the user and move them via a system of linkages, cables, or the like. Another device in the prior art comprises an exoskeleton that allows the user to move their legs, but which resists certain motions of the legs to keep the legs generally straight when necessary.

BRIEF SUMMARY OF THE INVENTION

An embodiment of the disclosure meets the needs presented above by generally comprising a waistband which is configured to extend around a body of the user. Each of a pair of leg attachment members is coupled to and extends downwardly from the waistband. Each leg attachment member is laterally positioned with respect to each other and comprises a leg panel and a leg strap. The leg panel is coupled to and extends downwardly from the waistband. The leg strap is coupled to and extends between a pair of lateral edges of the leg panel. The leg strap is configured for extending around one of a pair of legs of the user to attach the leg panel to the one leg. An electrical stimulator is coupled to each leg attachment member. The electrical stimulator comprises a plurality of electrical wires extending across each leg attachment member and a plurality of electrodes that is distributed across the plurality of electrical wires for transmitting electrical current through a skin of the user. The electrical stimulator is configured for selectively transmitting electrical signals to efferent nerves of the user to induce muscle contractions.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
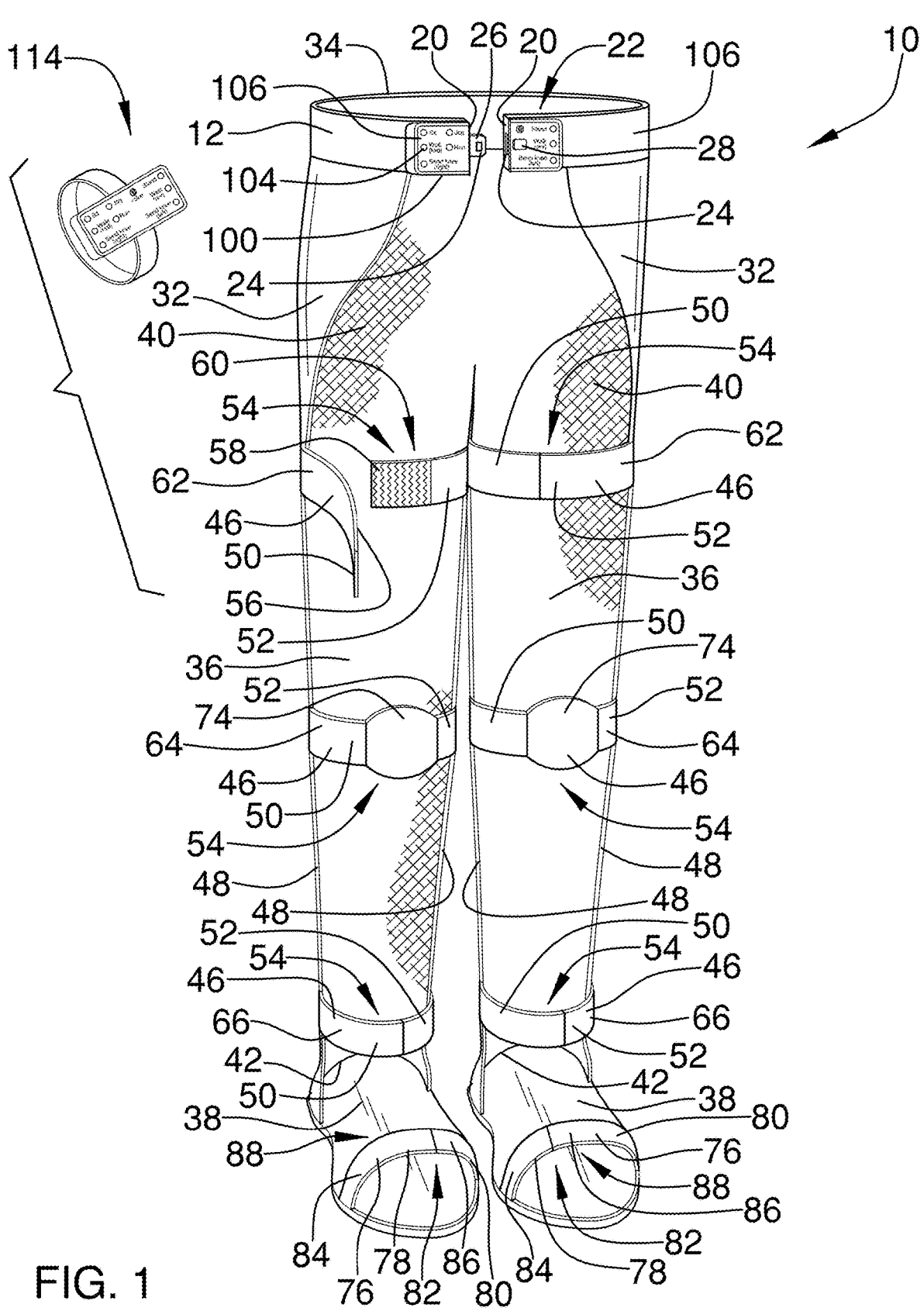
FIG. 1 is a front perspective view of a neuroprosthesis apparatus according to an embodiment of the disclosure.
Figure 2:
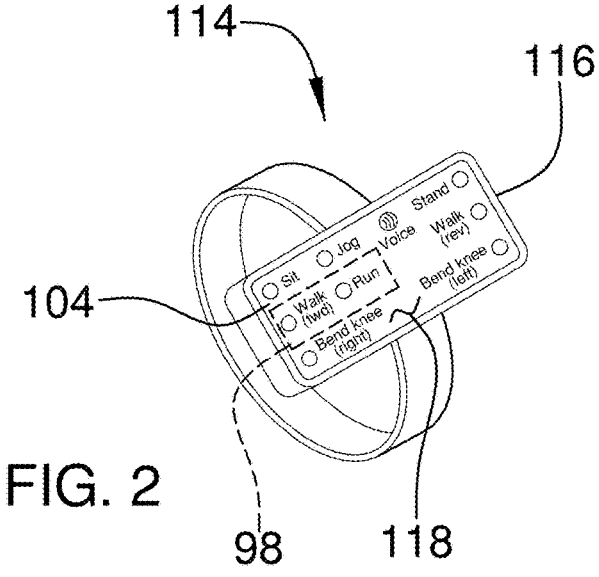
FIG. 2 is a perspective view of an armband of an embodiment of the disclosure.
Figure 3:
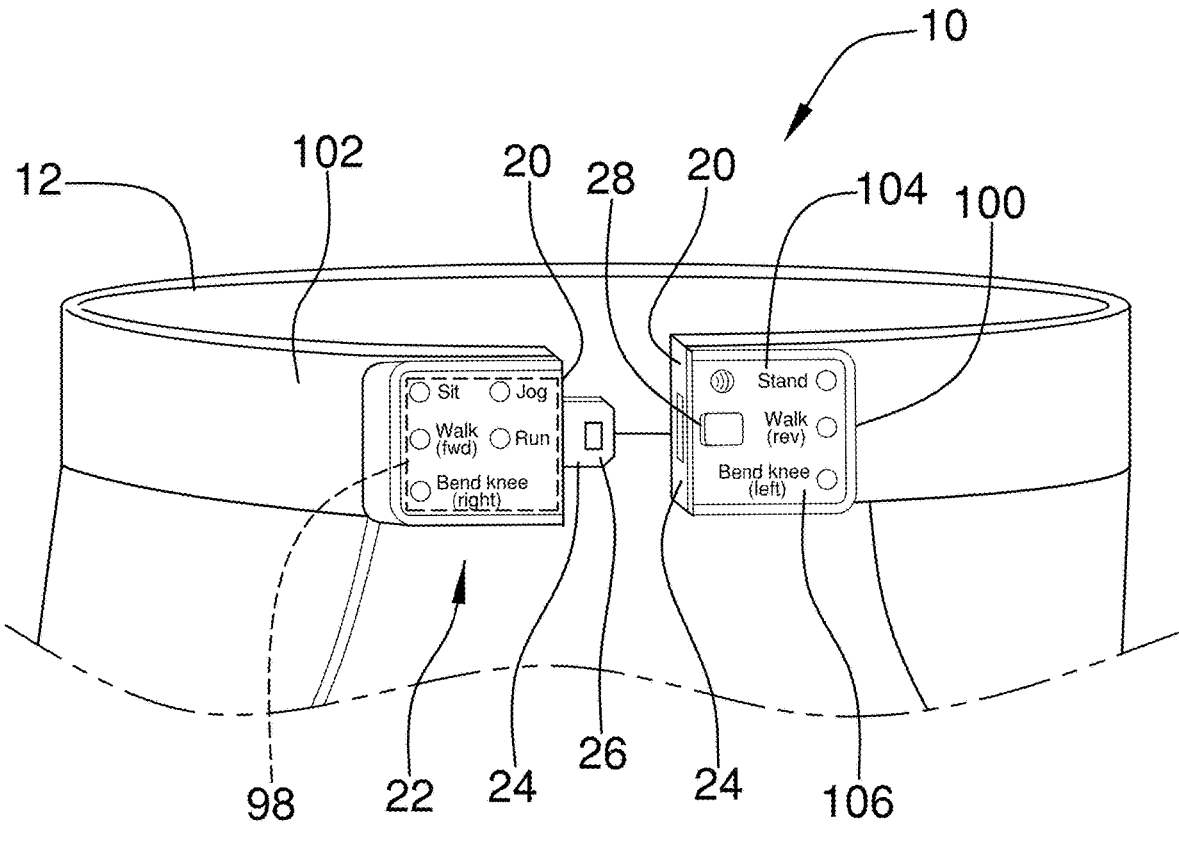
FIG. 3 is a detail perspective view of a waistband of an embodiment of the disclosure.
Figures 4, 5, 6:
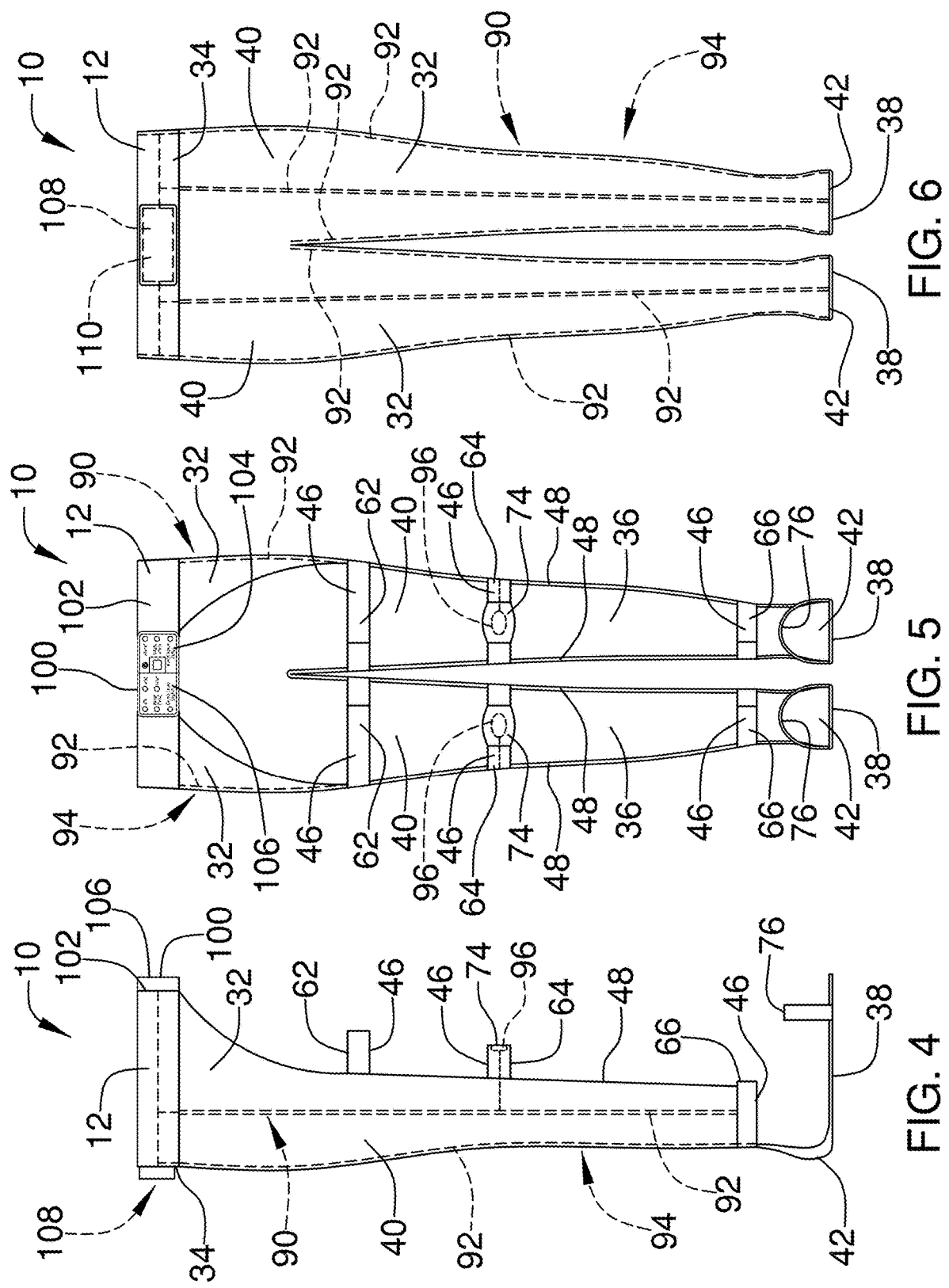
FIG. 4 is a side view of an embodiment of the disclosure.
FIG. 5 is a front view of an embodiment of the disclosure.
FIG. 6 is a rear view of an embodiment of the disclosure.
Figure 7:
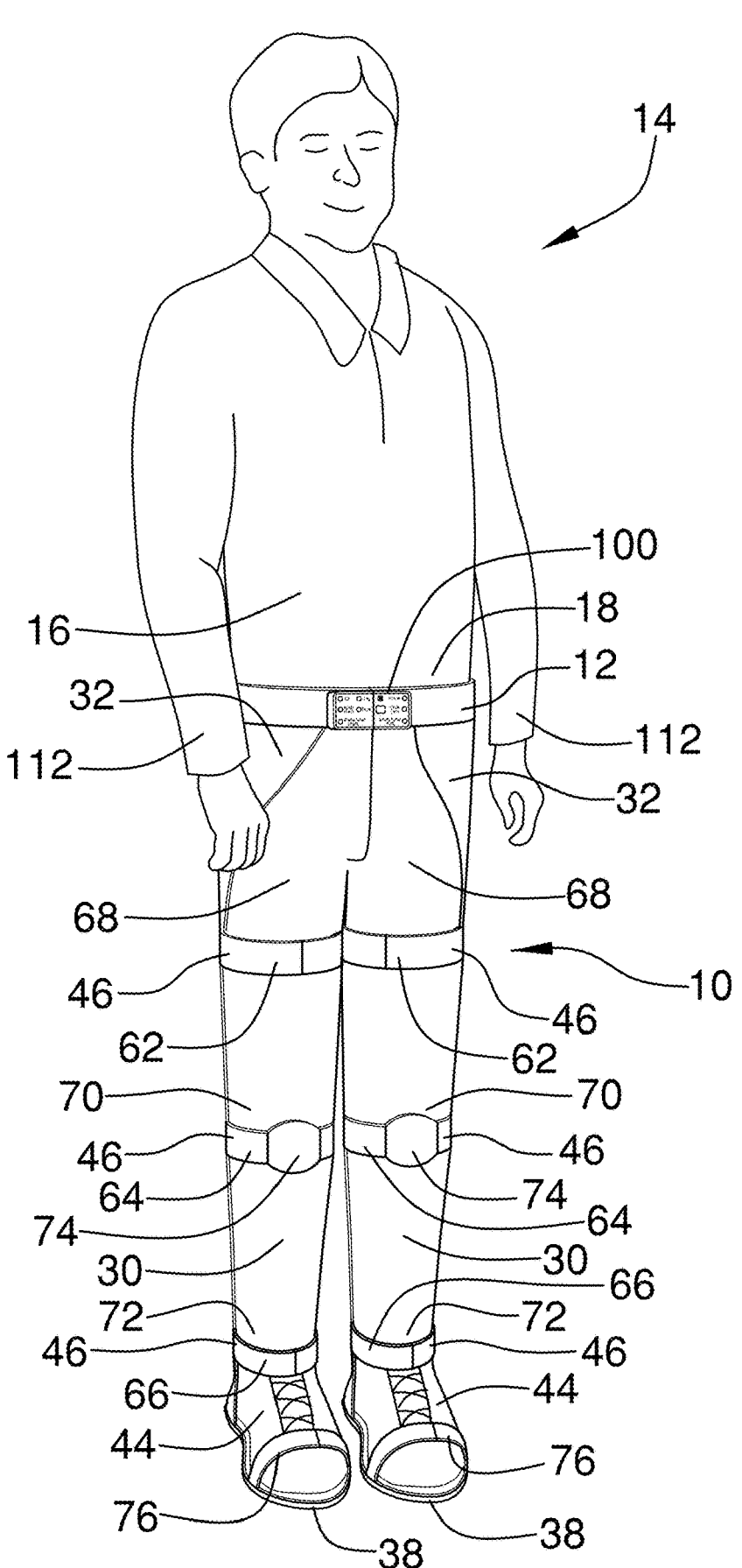
FIG. 7 is an in-use view of an embodiment of the disclosure.
Figure 8:
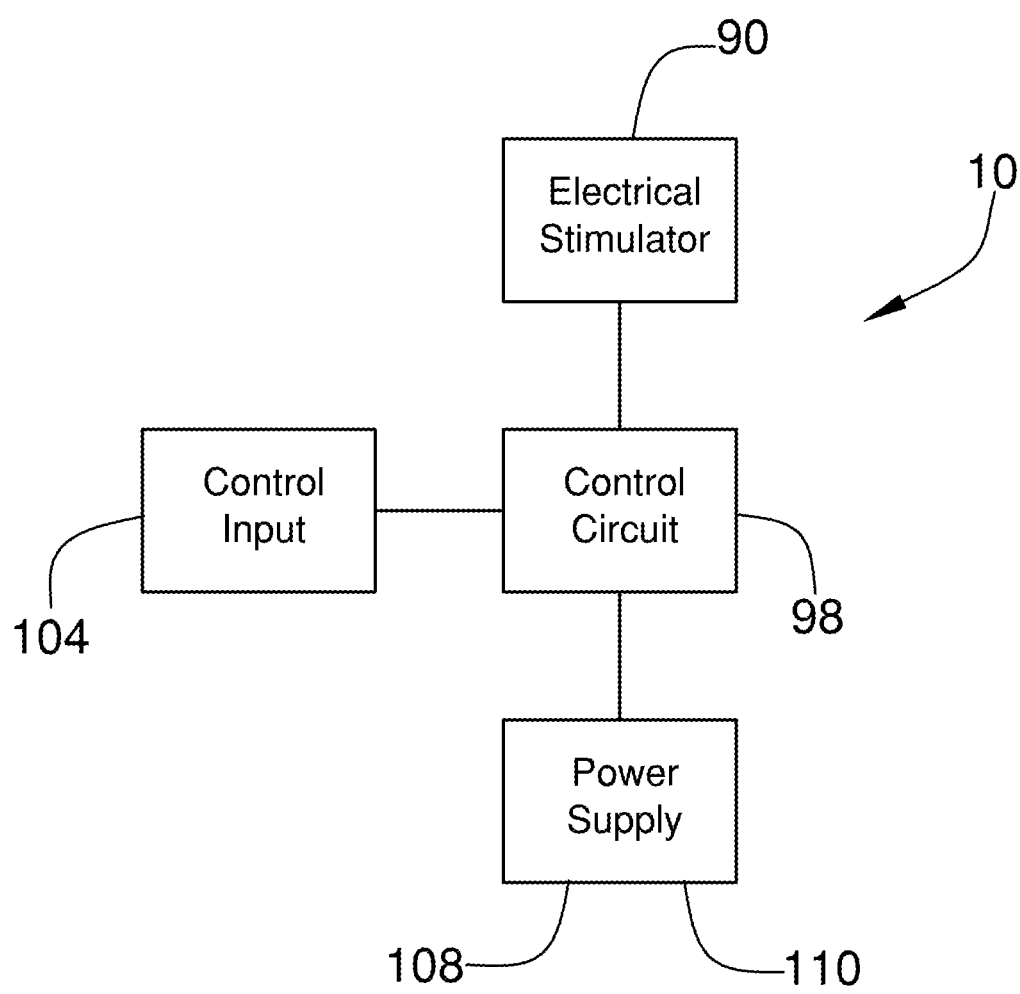
FIG. 8 is a block diagram of an embodiment of the disclosure.

With reference now to the drawings, and in particular to FIGS. 1 through 8 thereof, a new prosthesis embodying the principles and concepts of an embodiment of the disclosure and generally designated by the reference numeral 10 will be described.

As best illustrated in FIGS. 1 through 8, the neuroprosthesis apparatus 10 generally comprises a waistband 12 which is configured to extend around a body 16 of the user 14. The waistband 12 may be positioned to extend around the waist 18 of the user 14, the waist 18 being defined to include the hip. The waistband 12 may be elastic. The waistband 12 may be endless or may have a pair of ends 20, each of which is couplable to the other. In embodiments where the waistband 12 has a pair of ends 20, a pair of connecting elements 24 of a fastening member 22 is coupled to an associated one of the ends 20 of the waistband 12. One of the connecting elements 24 is a latch plate 26 and another of the connecting elements 24 is a spring-biased latching member 28 biased to engage the latch plate 26 to couple the pair of ends 20 of the waistband 12 together.

Each of a pair of leg attachment members 32 is coupled to and extends downwardly from the waistband 12. Each leg attachment member 32 is laterally positioned with respect to each other, and each leg attachment member 32 is coupled to each other adjacent to a rear side 34 of the waistband 12. Each leg attachment member 32 comprises a leg panel 40 which is coupled to and extends downwardly from the waistband 12 adjacent to the rear side 34. The leg panel 40 may be flexible and have a front surface 36 that is concave. A foot panel 38 may be coupled to and extend forwardly from the leg panel 40 adjacent to a bottom end 40 of the leg panel 40. The foot panel 38 has a top surface 42 which is configured for supporting one of a pair of feet 44 of the user 14 thereon. The foot panel 38 may also be rigid.

Each of a plurality of leg straps 46 is coupled to and extends between a pair of lateral edges 48 of the leg panel 40. Each leg strap 46 extends forwardly from the leg panel 40 and is configured for extending forwardly and around one of a pair of legs 30 of the user 14 to attach the leg panel 40 to the one leg 30. Each leg strap 46 comprises a first strap member 50 and a second strap member 52. A connector 54 is coupled to the leg strap 46 to releasably couple the first strap member 50 to the second strap member 52. A first mating element 56 of the connector 54 is attached to the first strap member 50, and a second mating element 58 of the connector 54 is attached to the second strap member 52. The first mating element 56 is releasably couplable to the second mating element 58. The connector 54 comprises a hook-and-loop fastener 60, but may comprise a button, buckle, snap fastener, or the like.

The plurality of leg straps 46 of each leg attachment member 32 includes a thigh strap 62, a knee strap 64, and an ankle strap 66. The thigh strap 62 is configured for attaching to a thigh 68 of the one leg 30. The knee strap 64 is positioned below the thigh strap 62 and is configured for attaching to a knee 70 of the one leg 30. The knee strap 64 also includes a knee pad 74 which is spaced forwardly of the leg panel 40. The knee pad 74 is configured for abutting the knee 70 of the user 14 when the knee strap 64 attaches to the knee 70 of the one leg 30. The ankle strap 66 is positioned below the knee strap 64 and is configured for attaching to an ankle 72 of the one leg 30.

A foot strap 76 is coupled to and extends between a pair of lateral edges 48 of the foot panel 38. The foot strap 76 extends upwardly from the foot panel 38 and is configured for extending upwardly and around one of a pair of feet 44 of the user 14 to attach the foot panel 38 to the one foot 44. The foot strap 76 comprises a first strap element 78 and a second strap element 80. A coupler 82 is attached to the foot strap 76 such that the first strap element 78 is releasably couplable to the second strap element 80. A first attaching element 84 of the coupler 82 is coupled to the first strap element 78, and a second attaching element 86 of the coupler 82 is attached to the second strap element 80. The first attaching element 84 is releasably couplable to the second attaching element 86. The coupler 82 comprises a hook-and-loop fastener 88, but may comprise a button, buckle, snap fastener, or the like.

An electrical stimulator 90 is coupled to each leg attachment member 32. The electrical stimulator 90 comprising a plurality of electrical wires 92 extending across each leg attachment member 32 and a plurality of electrodes 94 distributed across the plurality of electrical wires 92 for transmitting electrical current through a skin of the user 14. The electrical stimulator 90 extends across the leg panel 40 and the knee strap 64 of each leg attachment member 32. The electrical stimulator 90 is configured for selectively transmitting electrical signals to efferent nerves of the user 14 to induce muscle contractions. The plurality of electrodes 94 include a pair of knee electrodes 96, each of which is positioned on the knee pad 74 of each leg attachment member 32.

A control circuit 98 is electrically coupled to the electrical stimulator 90 but may be in signal communication with and unattached to the electrical stimulator 90. A housing 100 may be coupled to a front side 102 of the waistband 12. The housing 100 is hollow. The control circuit 98 may be coupled to and positioned within the housing 100. The fastening member 22 may also be integrated with the housing 100. A control input 104 is electrically coupled to the control circuit 98 and is configured for receiving commands from the user 14. The control input 104 selectively directs the control circuit 98 to actuate the electrical stimulator 90 in a selected one of a plurality of stimulation patterns. Each stimulation pattern is configured to transmit electrical signals such that one of the legs 30 and feet 44 moves. Complex stimulation patterns may be used to induce muscle contractions in the legs 30 and feet 44 to produce particular actions, including walking, running, sitting, standing, and the like. The control input 104 may be coupled to a front face 106 of the housing 100. A power supply 108 is electrically coupled to the control circuit 98 and comprises a battery 110. The power supply 108 is coupled to the rear side 34 of the waistband 12.

In some embodiments, the control circuit 98 and control input 104 may be incorporated onto an armband 114 configured for wearing on an arm 112 the user 14. The armband 114 generally includes a casing 116 with a forward face 118 configured for facing outwardly away from said arm 112 of said user 14. The control circuit 98 may be positioned within the casing 116 and the control input 104 may be coupled to and positioned on the forward face 118. In other embodiments, the control circuit 98 and control input 104 coupled to the housing 100 on the waistband 12 define a first control circuit and first control input respectively, while the armband 114 comprises a second control circuit and second control input for controlling the electrical stimulator 90.

In use, the neuroprosthesis apparatus 10 is worn by the user 14 by positioning the waistband 12 around the body 16 of the user 14, attaching each leg attachment member 32 to each leg 30 of the user 14. The user 14 enters commands via the control input 104 to induce muscle contractions in the user's 14 legs 30 and feet 44 as desired.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A neuroprosthesis apparatus for stimulating leg movement in a user via functional electrical stimulation (FES), the neuroprosthesis apparatus comprising:

a waistband, said waistband being configured to extend around a body of the user;

a pair of leg attachment members, each said leg attachment member being coupled to and extending downwardly from said waistband, each said leg attachment member being laterally positioned with respect to each other, each said leg attachment member comprising:

a leg panel, said leg panel being coupled to and extending downwardly from said waistband; and a leg strap being coupled to and extending between a pair of lateral edges of said leg panel, said leg strap being configured for extending around one of a pair of legs of the user to attach said leg panel to the one leg;

an electrical stimulator being coupled to each said leg attachment member, said electrical stimulator comprising a plurality of electrical wires extending across each said leg attachment member and a plurality of electrodes being distributed across said plurality of electrical wires for transmitting electrical current through a skin of the user, said electrical stimulator being configured for selectively transmitting electrical signals to efferent nerves of the user to induce muscle contractions; and an armband configured for wearing on an arm of the user, said armband including:

a casing;

a control circuit being in communication with to said electrical stimulator, said control circuit being coupled to and positioned within said casing; and a control input being electrically coupled to said control circuit, said control input being configured for receiving commands from the user, said control input selectively directing said control circuit to actuate said electrical stimulator in a selected one of a plurality of stimulation patterns, each said stimulation pattern being configured to transmit electrical signals such that one of the legs and feet moves, said control input being coupled to a forward face of said casing.

2. The apparatus of claim 1, further comprising said waistband being elastic.

3. The apparatus of claim 1, further comprising said waistband having a pair of ends, each of said pair of ends of said waistband being couplable to each other.

4. The apparatus of claim 3, further comprising a fastening member having a pair of connecting elements, each said connecting element being coupled to an associated one of said ends of said waistband.

5. The apparatus of claim 4, further comprising one of said connecting elements being a latch plate and another of said connecting elements being a spring-biased latching member biased to engage said latch plate.

6. The apparatus of claim 1, further comprising each said leg attachment member being coupled to each other adjacent to a rear side of said waistband.

7. The apparatus of claim 1, further comprising said leg panel of each said leg attachment member being coupled to said waistband adjacent to a rear side of said waistband.

8. The apparatus of claim 1, further comprising said leg panel of each said leg attachment member being flexible.

9. The apparatus of claim 7, further comprising said leg panel of each said leg attachment member having a front surface being concave.

10. The apparatus of claim 1, further comprising said leg strap comprising a first strap member and a second strap member, each said leg strap including a connector having a first mating element being coupled to said first strap member and a second mating element being coupled to said second strap member, said first mating element being releasably couplable to said second mating element.

11. The apparatus of claim 10, further comprising said connector comprising a hook-and-loop fastener.

12. The apparatus of claim 1, further comprising said leg strap of each said leg attachment member being one of a plurality of leg straps, each said leg strap being coupled to and extending between said pair of lateral edges of said leg panel of an associated one of said pair of leg attachment members, each said leg strap being configured for extending around the one leg of the user to attach said leg panel to the one leg.

13. The apparatus of claim 12, further comprising said plurality of leg straps of each said leg attachment member including a thigh strap being configured for attaching to a thigh of the one leg, a knee strap being positioned below said thigh strap, said knee strap being configured for attaching to a knee of the one leg, an ankle strap being positioned below said knee strap, said ankle strap being configured for attaching to an ankle of the one leg.

14. The apparatus of claim 13, further comprising said knee strap of each said leg attachment member including a knee pad, said knee pad being spaced forwardly of said leg panel of said associated one of said pair of leg attachment members, said knee pad being configured for abutting the knee of the user when said knee strap attaches to the knee of the one leg.

15. The apparatus of claim 14, further comprising said plurality of electrodes including a pair of knee electrodes, each knee electrode being positioned on said knee pad of each said leg attachment member.

16. The apparatus of claim 1, further comprising each said leg attachment member further comprising:

a foot panel being coupled to and extending forwardly from said leg panel adjacent to a bottom end of said leg panel, said foot panel having a top surface, said top surface being configured for supporting a foot of the user thereon; and a foot strap being coupled to and extending between a pair of lateral edges of said foot panel, said foot strap extending upwardly from said foot panel, said foot strap being configured for extending upwardly and around one of a pair of feet of the user to attach said foot panel to the one foot.

17. The apparatus of claim 16, further comprising said foot panel of each said leg attachment member being rigid.

18. The apparatus of claim 1, further comprising:

a housing being coupled to a front side of said waistband, said housing being hollow;

a first control circuit being electrically coupled to said electrical stimulator, said first control circuit being coupled to and positioned within said housing; and a first control input being electrically coupled to said first control circuit, said first control input being configured for receiving commands from the user, said first control input selectively directing said first control circuit to actuate said electrical stimulator in said selected one of said plurality of stimulation patterns, each said stimulation pattern being configured to transmit electrical signals such that one of the legs and feet moves, said control input being coupled to a front face of said housing;

wherein said control circuit within said casing of said armband is a second control circuit and said control input on said casing of said armband is a second control input.

19. The apparatus of claim 18, further comprising a power supply being electrically coupled to said first control circuit, said power supply comprising a battery, said power supply being coupled to said rear side of said waistband.

20. A neuroprosthesis apparatus for stimulating leg movement in a user via functional electrical stimulation (FES), the neuroprosthesis apparatus comprising:

a waistband, said waistband being configured to extend around a body of the user, said waistband being elastic, said waistband having a pair of ends, each of said pair of ends of said waistband being couplable to each other;

a pair of leg attachment members, each said leg attachment member being coupled to and extending downwardly from said waistband, each said leg attachment member being laterally positioned with respect to each other, each said leg attachment member being coupled to each other adjacent to a rear side of said waistband, each said leg attachment member comprising:

a leg panel, said leg panel being coupled to and extending downwardly from said waistband adjacent to said rear side, said leg panel being flexible, said leg panel having a front surface being concave;

a foot panel being coupled to and extending forwardly from said leg panel adjacent to a bottom end of said leg panel, said foot panel having a top surface, said top surface being configured for supporting a foot of the user thereon, said foot panel being rigid;

a plurality of leg straps, each said leg strap being coupled to and extending between a pair of lateral edges of said leg panel, each said leg strap extending forwardly from said leg panel, each said leg strap being configured for extending forwardly and around one of a pair of legs of the user to attach said leg panel to the one leg, each said leg strap comprising a first strap member and a second strap member, said first strap member being releasably couplable to said second strap member, each said leg strap including a connector having a first mating element being coupled to said first strap member and a second mating element being coupled to said second strap member, said first mating element being releasably couplable to said second mating element, said connector comprising a hook-and-loop fastener, said plurality of leg straps including:

a thigh strap being configured for attaching to a thigh of the one leg;

a knee strap being positioned below said thigh strap, said knee strap being configured for attaching to a knee of the one leg, said knee strap including a knee pad, said knee pad being spaced forwardly of said leg panel, said knee pad being configured for abutting the knee of the user when said knee strap attaches to the knee of the one leg; and an ankle strap being positioned below said knee strap, said ankle strap being configured for attaching to an ankle of the one leg; and a foot strap being coupled to and extending between a pair of lateral edges of said foot panel, said foot strap extending upwardly from said foot panel, said foot strap being configured for extending upwardly and around one of a pair of feet of the user to attach said foot panel to the one foot, said foot strap comprising a first strap element and a second strap element, said first strap element being releasably couplable to said second strap element, said foot strap including a coupler having a first attaching element being coupled to said first strap element and a second attaching element being coupled to said second strap element, said first attaching element being releasably couplable to said second attaching element, said coupler comprising a hook-and-loop fastener;

an electrical stimulator being coupled to each said leg attachment member, said electrical stimulator comprising a plurality of electrical wires extending across each said leg attachment member and a plurality of electrodes being distributed across said plurality of electrical wires for transmitting electrical current through a skin of the user, said electrical stimulator extending across said leg panel and said knee strap of each said leg attachment member, said electrical stimulator being configured for selectively transmitting electrical signals to efferent nerves of the user to induce muscle contractions, said plurality of electrodes including a pair of knee electrodes, each knee electrode being positioned on said knee pad of each said leg attachment member;

a housing being coupled to a front side of said waistband, said housing being hollow;

a first control circuit being electrically coupled to said electrical stimulator, said first control circuit being coupled to and positioned within said housing;

a first control input being electrically coupled to said first control circuit, said first control input being configured for receiving commands from the user, said first control input selectively directing said first control circuit to actuate said electrical stimulator in a selected one of a plurality of stimulation patterns, each said stimulation pattern being configured to transmit electrical signals such that one of the legs and feet moves, said first control input being coupled to a front face of said housing;

a fastening member having a pair of connecting elements, each said connecting element being coupled to an associated one of said ends of said waistband, one of said connecting elements being a latch plate and another of said connecting elements being a spring-biased latching member biased to engage said latch plate, said fastening member being integrated with said housing;

a power supply being electrically coupled to said control circuit, said power supply comprising a battery, said power supply being coupled to said rear side of said waistband; and an armband configured for wearing on an arm of the user, said armband including:

a casing;

a second control circuit being electrically coupled to said electrical stimulator, said second control circuit being coupled to and positioned within said casing; and a second control input being electrically coupled to said second control circuit, said second control input being configured for receiving commands from the user, said second control input selectively directing said second control circuit to actuate said electrical stimulator in said selected one of said plurality of stimulation patterns, each said stimulation pattern being configured to transmit electrical signals such that one of the legs and feet moves, said second control input being coupled to a forward face of said casing.

\* \* \* \* \*